United States Patent
Cornsweet et al.

(10) Patent No.: US 10,182,716 B2
(45) Date of Patent: Jan. 22, 2019

(54) SYSTEMS, METHODS AND DEVICES FOR MONITORING EYE MOVEMENT TO TEST A VISUAL FIELD

(71) Applicant: Brien Holden Vision Institute, Sydney (AU)

(72) Inventors: Tom N. Cornsweet, Prescott, AZ (US); Paul Peterson, Prescott, AZ (US); Brad Bower, Hillsborough, NC (US)

(73) Assignee: Brien Holden Vision Institute, Sydney, New South Wales (AU)

(*) Notice: Subject to any disclaimer, the term of this patent is extended or adjusted under 35 U.S.C. 154(b) by 0 days.

(21) Appl. No.: 15/505,511

(22) PCT Filed: Aug. 19, 2015

(86) PCT No.: PCT/US2015/045865
§ 371 (c)(1),
(2) Date: Feb. 21, 2017

(87) PCT Pub. No.: WO2016/028877
PCT Pub. Date: Feb. 25, 2016

(65) Prior Publication Data
US 2017/0265737 A1 Sep. 21, 2017

Related U.S. Application Data

(60) Provisional application No. 62/040,522, filed on Aug. 22, 2014.

(51) Int. Cl.
*A61B 3/024* (2006.01)
*A61B 3/113* (2006.01)
(Continued)

(52) U.S. Cl.
CPC ............ *A61B 3/024* (2013.01); *A61B 3/0058* (2013.01); *A61B 3/06* (2013.01); *A61B 3/113* (2013.01); *A61B 5/7275* (2013.01); *A61B 5/7282* (2013.01)

(58) Field of Classification Search
CPC ....... A61B 3/113; A61B 3/0025; A61B 3/112; G06K 9/00604; G06K 9/00597
(Continued)

(56) References Cited

U.S. PATENT DOCUMENTS 5,114,222 A * 5/1992 Cornsweet ............. A61B 3/112
351/204
7,918,558 B1 * 4/2011 Legerton ............... A61B 3/0033
351/211
(Continued)

FOREIGN PATENT DOCUMENTS

JP 2003164425 6/2003
WO WO 99/22638 5/1999
(Continued)

OTHER PUBLICATIONS

International Search Report dated Nov. 24, 2015 for PCT/US2015/045865.

*Primary Examiner* — Mohammed Hasan
(74) *Attorney, Agent, or Firm* — Jones Day (57) ABSTRACT

A method for evaluating retinal function and testing the visual field of a patient by monitoring how the patient tracks a target image on a display that comprises displaying the target image on the display such that it is located at a first position on the display and visible to the patient. The process continues by identifying what portion of the display the patient is looking at, selecting a location of the patient's retina to test, and calculating, based at least in part on what portion of the display the patient is looking at, a second position on the display corresponding to the selected loca- (Continued)

tion of the patient's retina. The target image is displayed at the second position on the display and the process identifies how many eye movements the patient made to look at the target at the second position. Based at least in part on the number of eye movements, the process determines whether the patient was able to see the target at the second position.

20 Claims, 4 Drawing Sheets

(51) Int. Cl.
      *A61B 3/06*       (2006.01)
      *A61B 5/00*       (2006.01)
      *A61B 3/00*       (2006.01)

(58) Field of Classification Search
      USPC .................................................. 351/200–246
      See application file for complete search history.

(56) References Cited

U.S. PATENT DOCUMENTS

| | | |
|---|---|---|
| 2010/0039617 A1 | 2/2010 | Martinez-Conde et al. |
| 2011/0006978 A1 | 1/2011 | Yuan |
| 2012/0081666 A1* | 4/2012 | Kiderman .............. A61B 3/113 351/210 |

FOREIGN PATENT DOCUMENTS

| | | |
|---|---|---|
| WO | WO 2006/106877 | 10/2006 |
| WO | WO 2008/139137 | 11/2008 |
| WO | WO 2013/102768 | 7/2013 |

* cited by examiner

SYSTEMS, METHODS AND DEVICES FOR MONITORING EYE MOVEMENT TO TEST A VISUAL FIELD

CROSS REFERENCE TO RELATED APPLICATION

This application is the National Phase application of International Application No. PCT/US2015/045865, filed Aug. 19, 2015, which claims priority to U.S. Provisional Application No. 62/040,522, filed on Aug. 22, 2014. This application is also related to U.S. Provisional Application No. 61/937,788, filed on Feb. 10, 2014; U.S. application Ser. No. 13/409,056, filed on Feb. 29, 2012; International Application No. PCT/US2012/027161, filed on Feb. 29, 2012; U.S. Provisional Application No. 61/448,342, filed Mar. 2, 2011; and U.S. Provisional Application No. 61/874,651, filed Sep. 6, 2013. Each of the foregoing applications, in their entirety, are herein incorporated by reference.

TECHNICAL FIELD

This document generally relates to systems, methods, and devices for monitoring eye movement to test a visual field. More specifically, the disclosure relates to systems, methods, and devices for performing perimetry (visual field) tests without requiring subjective patient interaction.

BACKGROUND

Conventionally, a device referred to as a perimeter is used to perform a visual field test on a patient. The perimetry test measures the patient's eyesight throughout the visual field (e.g, central and peripheral).

During the test, the patient is asked to look into the perimeter device and look forward at the center of the illuminated area. The device is configured to flash a light on to different areas of the display and when the patient sees the flash of light, the patient is asked to press a button (or in some way acknowledge they have seen the light). The device records the location of the flash and whether the patient indicated they saw the flash and creates a map of the patients eye indicating where the patient was able to see the flash and where they were not able to see the flash.

This, and other known methods, have a number of draw backs. For example, because the patient is asked to indicate when they see the flash while they are looking at a different place, the task is difficult and stressful, and there is a significant margin for error.

Accordingly, it is desirable to have systems, methods, and devices for performing perimetry tests without requiring subjective patient interaction and/or decision making.

SUMMARY OF EMBODIMENTS

In exemplary embodiments, perimetry may be used to evaluate retinal function through visual field testing without the need for subjective feedback from the patient, thereby inferring information by analyzing the patient's eye movements.

Exemplary embodiments may provide for a method for evaluating retinal function and testing the visual field of a patient by monitoring how the patient tracks a target image on a display, the method comprising: displaying the target image on the display, the target image being located at a first position on the display such that it is visible to the patient; identifying what portion of the display the patient is looking at; selecting a location of the patient's retina to test; calculating, based at least in part on what portion of the display the patient is looking at, a second position on the display corresponding to the selected location of the patient's retina; displaying the target image at the second position on the display; identifying how many eye movements the patient made to look at the target at the second position; and determining, based at least in part on the number of eye movements, whether the patient was able to see the target at the second position.

In exemplary embodiments, the target image may be a point light source and the display may be an array of LEDs configured such that different combinations of LEDS are illuminated to present a target image at different locations. In general, the target image may be any acceptable image and the display may be any device capable of displaying the target image to the patient.

In exemplary embodiments, the selection of the location on the patient's retina may be perceived as being random by the patient.

In exemplary embodiments, the process continues by displaying the target image at a predetermined plurality of positions on the display corresponding to predetermined positions of the patient's retina until a map of the patient's retina is achieved.

In exemplary embodiments, if the patient makes a single eye movement (e.g., a single saccade that hits close to the target location and is confirmed by tracking the gaze within that "accurate" radius around the target location) to look at the target at the second position with a selected degree of accuracy from the first position, the determination is made that the patient was able to see the target at the second position and that the corresponding portion of the retina is healthy.

In exemplary embodiments, if the patient makes more than one eye movement to look at the target at the second position from the first position, the determination is made that the patient was not able to see the target at the second position and that the corresponding area of the retina is not healthy.

In exemplary embodiments, more than one eye movement may correspond to more than one eye movement in a predetemiined time. For example, in exemplary embodiments, more than one eye movement may correspond to more than one eye movement in about 2 seconds, or more than one eye movement in about 1 second, or more than one eye movement in about 1.5 seconds, or more than one eye movement in about 2.5 seconds, or more than one eye movement in about 3 seconds, or more than one eye movement in about 4 seconds.

In exemplary embodiments, if the patient does not make any eye movement, (e.g., any eye movement exceeding a predetermined threshold), the determination may be made that the patient was not able to see the target at the second position and that the corresponding area of the retina is not healthy In exemplary embodiments, if the patient makes more than one eye movement to look at the target at the second position from the first position, the process re-tests the second position on the retina of the patient at some subsequent step in the procedure.

In exemplary embodiments, if the patient makes more than one eye movement to look at the target at the second position from the first position, the process identifies the intermediary positions where the patient was looking and determines, based at least in part on the next eye movement, whether the patient was able to see the target when the eye was at the intermediary positions.

In exemplary embodiments, the process may also comprise adjusting the distance of the display relative to the patient to focus the target.

In exemplary embodiments, the target may jump from the first position on the display to the second position on the display.

In exemplary embodiments, the target may jump from the first position on the display to the second position on the display after about 0.2, 0.3, 0.4, 0.5, 0.6, 0.7, 0.8, 0.9, 1, 1.25, 1.5, 1.75, 2, 3, 4, 5, 6, 7, 8, 9, or 10 seconds.

In exemplary embodiments, the diameter of the area of the patient's retina that is measurable may be about twice the diameter of the patient's field of view on the display.

In exemplary embodiments, there may only be one target on the display at a time.

In exemplary embodiments, any combination of the brightness, size, shape, color, or background of the target may be variable.

In exemplary embodiments, the process may be used, at least in part, to aid with diagnosing and/or monitoring progression of glaucoma.

In exemplary embodiments, the process may be used, at least in part, to aid with diagnosing and/or monitoring progression of retinal artery or vein occlusion.

In exemplary embodiments, the process may be used, at least in part, to aid with diagnosing and/or monitoring progression of hemianopsia and optic tract glioma.

In exemplary embodiments, the process may be used, at least in part, to aid with diagnosing and/or monitoring progression of retinal detachment.

Exemplary embodiments may provide for a device for evaluating retinal function and testing the visual field of a patient by monitoring how the patient tracks a target image on a display, the device comprising: a display configured to display the target image on the display, the target image being located at a first position on the display such that it is visible to the patient; at least one camera assembly configured to image the patient's eye to identify what portion of the display the patient is looking at; and a processor configured to control the display and the camera and to analyze the data obtained from the at least one camera; wherein the processor is configured to: (i) select a location of the patient's retina to test; (ii) calculate, based at least in part on what portion of the display the patient is looking at, a second position on the display corresponding to the selected location of the patient's retina; (iii) display the target image at the second position on the display; (iv) identify how many eye movements the patient made to look at the target at the second position; and (v) determine, based at least in part on the number of eye movements, whether the patient was able to see the target at the second position.

In exemplary embodiments, the selection of the location on the patient's retina may be perceived as being random by the patient.

In exemplary embodiments, the processor may be configured to continue displaying the target image at a predetermined plurality of positions on the display corresponding to predetermined positions of the patient's retina until a map of the patient's retina is achieved.

In exemplary embodiments, if the patient makes a single eye movement to look at the target at the second position from the first position, the determination may be made that the patient was able to see the target at the second position and that the corresponding portion of the retina was healthy.

In exemplary embodiments, if the patient makes more than one eye movement to look at the target at the second position from the first position, the determination may be made that the patient was not able to see the target at the second position and that the corresponding portion of the retina was healthy.

In exemplary embodiments, if the patient makes more than one eye movement to look at the target at the second position from the first position, the processor may be configured to re-test the second position on the retina of the patient.

In exemplary embodiments, if the patient makes more than one eye movement to look at the target at the second position from the first position, the processor may be configured to identify the intermediary positions where the patient was looking and determine, based at least in part on the next eye movement, whether the patient was able to see the target when the eye was at the intermediary positions.

In exemplary embodiments, the position of the display may be adjustable relative to the patient to aid with focusing the target.

In exemplary embodiments, the target may jump from the first position on the display to the second position on the display.

In exemplary embodiments, the target may jump from the first position on the display to the second position on the display after about 0.2, 0.3, 0.4, 0.5, 0.6, 0.7, 0.8, 0.9, 1, 1.25, 1.5, 1.75, 2, 3, 4, 5, 6, 7, 8, 9, or 10 seconds.

In exemplary embodiments, the area of the patient's retina that is measurable may be about twice the diameter of the patient's field of view on the display.

In exemplary embodiments, there may only be one target on the display at a time.

In exemplary embodiments, any combination of the brightness, size, shape, color, or background of the target may be variable.

In exemplary embodiments, the device may be used, at least in part, to aid with diagnosing and/or monitoring progression of glaucoma.

In exemplary embodiments, the device may be used, at least in part, to aid with diagnosing and/or monitoring progression of diabetic retinpathy.

In exemplary embodiments, the device may be used, at least in part, to aid with diagnosing and/or monitoring progression of retinal artery or vein occlusion.

In exemplary embodiments, the device may be used, at least in part, to aid with diagnosing and/or monitoring progression of hemianopsia and optic tract glioma.

In exemplary embodiments, the device may be used, at least in part, to aid with diagnosing and/or monitoring progression of retinal detachment.

DESCRIPTION OF THE DRAWINGS

Notwithstanding any other forms which may fall within the scope of the disclosure as set forth herein, specific embodiments will now be described by way of example and with reference to the accompanying drawings in which.

DETAILED DESCRIPTION OF EXEMPLARY EMBODIMENTS

This document describes methods, systems and devices for using eye movement perimetry to evaluate retinal function through visual field testing without the need for subjective feedback from the patient, thereby inferring information by analyzing the patient's eye movements. The concept of eye-movement perimetry may be more easily understood if certain common terms are initially explained.

In exemplary embodiments, the term "grid" may be utilized to describe a set of locations across the visual field of a patient's retina. In exemplary embodiments the grid may be designed for a particular purpose (e.g., screening for glaucoma).

In exemplary embodiments, a "session" may refer to the perimetry related activity that occurs for a particular patient. For example, in exemplary embodiments, a session may encompass all of the perimetry related activities during a patient's visit and may involve one or more tests. Similarly, tests may be more specific in their design (i.e., a quick glaucoma test) and composed of a sequence of trials.

In exemplary embodiments, the term "target" may be used to describe a visible dot (or other shape) on a display that is viewed by the patient. As described herein, in exemplary embodiments, only one target may be presented at a time. In exemplary embodiments, the target may jump to/from various parts of the display.

In exemplary embodiments, the term "test" may refer to a sequence of trials that are executed to move the target across multiple (e.g., many or all) positions on the display specified by a selected grid.

In exemplary embodiments, the term "trial" may refer to a time interval starting with the subject fixated on the target, and ending when the target jumps to a new location and the subject successfully finds and fixates on the new target via one or more eye movements (i.e., saccades).

In exemplary embodiments, a purpose of eye movement perimetry may be to perform automated perimetry. Accordingly, in exemplary embodiments, a patient may look into a device and through a lens at a target presented on a display, for example an LCD display. The distance between the lens and the display may be adjusted so that the target appears reasonably sharp. The operator of the device may then start a preliminary training period, during which the target jumps abruptly from one location on the display to another location on the display in an apparently random pattern. The patient may be asked to keep looking directly at the target and to follow it with their eyes. In exemplary embodiments, during training, an indication (e.g., an audio or visual indication) may be presented that indicates whether or not the patient is correctly fixating on the spot.

After the target is displayed for a fixed interval, e.g., 0.2, 0.3, 0.4, 0.5, 0.6, 0.7, 0.8, 0.9, 1, 1.25, 1.5, 1.75, 2, 3, 4, 5, 6, 7, 8, 9, or 10 seconds, the device may determine where the patient is looking on the display. Utilizing this information, the device may determine where on the display the target should jump to so that the image of the target falls on a retinal location that is intended to be tested next. In exemplary embodiments, the target may move, instantaneously (or very quickly), to a new position on the display. In exemplary embodiments, the target may be referred to as "jumping" from one position on the display to another. As would be readily understood, this may be accomplished in a variety of manners. For example, the target may be illuminated at one position of the display and then after it is turned off at that position of the display, illuminated on a second position of the display. Alternatively, the target may be illuminated at the second position of the display before it is turned off on the first portion of the display. In either case, the perception is that the target is "jumping" from one position to another. Further, in exemplary embodiments there may not be more than one target on the display at any given time. In exemplary embodiments, the target may not be displayed for a fixed interval. Instead, it may be displayed until the patient has been correctly looking at the target position for some fixed interval, e.g., 0.2, 0.3, 0.4, 0.5, 0.6, 0.7, 0.8, 0.9, 1, 1.25, 1.5, 1.75, 2, 3, 4, 5, 6, 7, 8, 9, or 10 seconds. For example, if a patient requires more than one saccade to reach the target, the time before the next target may be longer.

As will be appreciated by persons of ordinary skill in the art, there is a difference between having the target merely move among fixed places on the display and among places on the display that will test the desired spots on the retina.

In general, where the patient is looking (or fixating) may be described as the eye being rotated to a position such that the image or point that the patient is looking at falls on the fovea of the patient's eye. As would be understood by a person of ordinary skill in the art, there is a tiny region, near the center of the retina, called the fovea, where the highest density of photoreceptor cells exists. When a target is displayed at a point at a different place than where he or she is currently looking, the image of the point will fall somewhere on the retina away from the fovea. As a result, the visual system will determine a new set of tensions that the eye muscles (six on each eye) must take up to cause the eye to rotate to the correct position, the muscles are instructed to change their tensions accordingly and the eye rotates such that the retina slides beneath the image of the new point. When the movement or movement series is complete, the image of the new point falls on the fovea once again.

When a target jumps from its current location to a new location, a typical reaction time may be about 200 milliseconds. That is, about 200 ms elapse between the time the target first jumps and the time the patient begins to make a corresponding eye movement. If the retinal region that the image of the target falls on before the eye movement occurs is healthy, the patient may make a fast, single, ballistic eye movement (called a saccade), which will cause the retina to slide under the image of the target, and when the saccade ends, the patient will be looking at the new target position. However, if the target fell on a blind spot, the patient may make a saccadic movement to some location different from the target position, which will move the image of the target to a different retinal location. If, after that movement, the target falls on healthy retina, the patient may make a second saccadic movement such that he or she will be looking at the new target position.

Exemplary embodiments described herein may utilize a device capable of performing the perimetry methods described. For example, in embodiments, a device that generates the target to an eye while monitoring and/or measuring the resulting eye movements may be provided. The resulting eye movements may be analyzed by a processor and the analysis may be performed in real time or substantially real time.

In exemplary embodiments, the device may consist of three main components or subsystems. One subsystem may be responsible for display of the targets on a display. Another subsystem may monitor movement of the eye. The third subsystem may be a computer/processor and/or software that controls the first two subsystems, analyzes the results, and/or provides a user interface.

Figure 1:
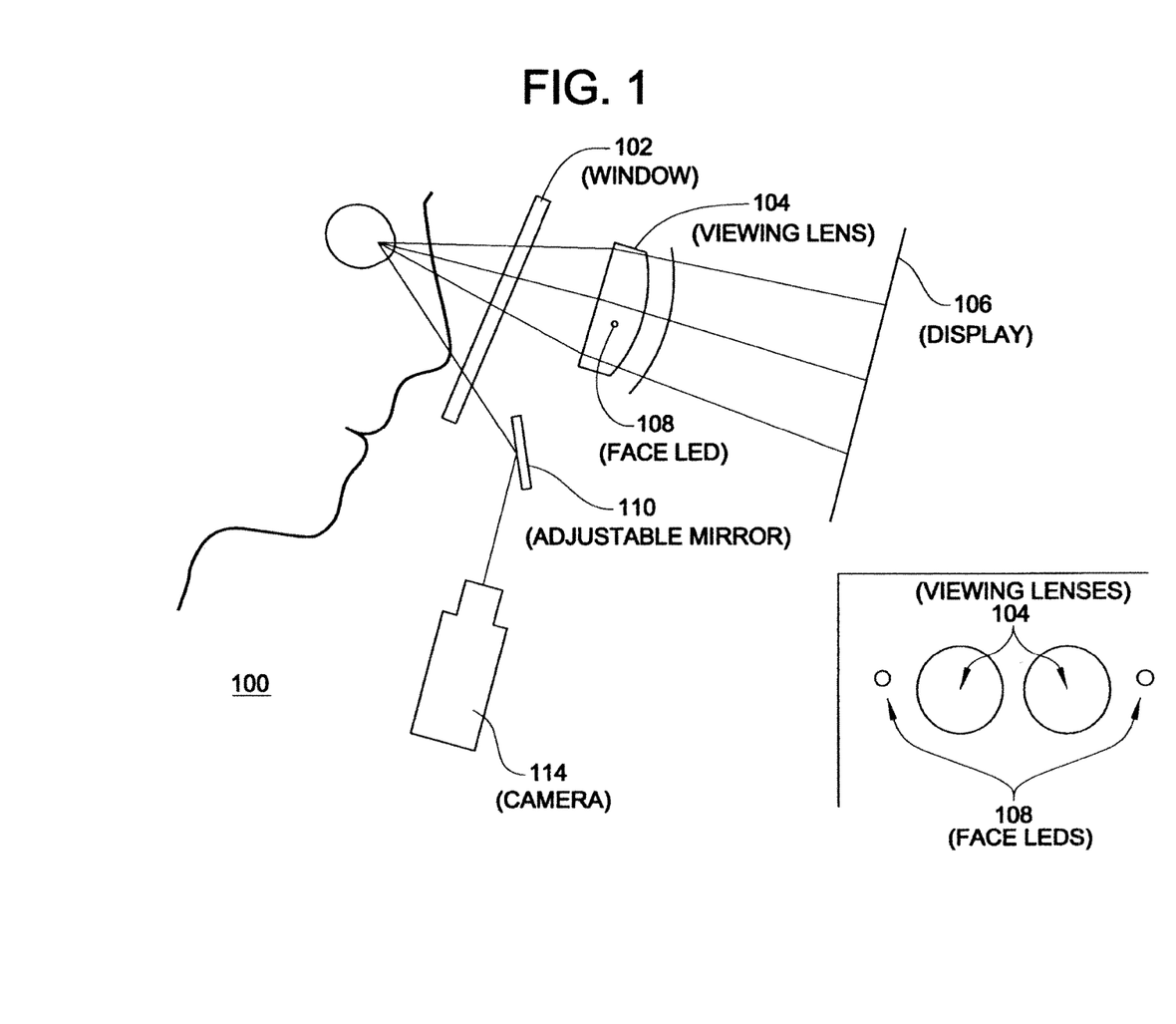
FIG. 1 is a schematic diagram of an exemplary device for use in monitoring and/or measuring eye movement in response to stimuli provided on a display.

FIG. 1 is a schematic diagram of an exemplary device for use in monitoring and/or measuring eye movement in response to stimuli provided on a display. As illustrated, the device 100 is configured to allow an individual to look into the device via a window 102. When the individual looks into the device, the individual looks through a viewing lens 104 and at a display 106. The display 106 may be moved relative to the viewing lens 104. In addition, the device 100 may comprise one or more LEDs 108 for illuminating the eye or eyes of the individual. In exemplary embodiments, the LED(s) 108 may be located adjacent to the viewing lens 104. In exemplary embodiments, one or more LEDs may be provided for the eye. In exemplary embodiments, the LEDs may be infrared LEDs.

In exemplary embodiments, the LED(s) may illuminate the individual's eyes and a portion of the light may be reflected from the eyes and onto mirror 110. In exemplary embodiments, the mirror 110 may be an adjustable mirror 110. The light may then be captured by a camera 114. The images captured by the camera may be sent to a computer/processor for analysis. In exemplary embodiments, the adjustable mirror 110 may be driven by a motor (not shown) to rotate the adjustable mirror 110 about a substantially horizontal axis through the center of the adjustable mirror 110 and a second motor (not shown) may rotate the mirror about an axis at 90 degrees to the horizontal and in the plane of the mirror. In exemplary embodiments, the motor may be driven by the computer/processor to adjust the image as necessary. For example, the computer may adjust the motor such that the image of the pupil is roughly centered in the camera view. In exemplary embodiments, this may compensate for patients whose eyes are higher or lower with respect to the nose bridge.

Additionally, in exemplary embodiments, the optical system, including e.g., the display, may be driven by another motor (not shown) towards and/or away from the individual, to focus the images of the pupils, as desired.

In exemplary embodiments, the display may be moved relative to the viewing lens.

As may be appreciated from the above description, in exemplary embodiments, the field of view of the patient in the instrument/device may be limited in size by the optics between the eye and the display, and by the distance between the optics and the eye. For example, in exemplary devices the field of view may be limited to 30 degrees. However, the region of the retina that can be mapped in this way is twice the diameter of the patient's field of view.

For example, suppose that a patient is looking at the center of a 30 degree field and the target jumps horizontally to the edge of the field—a 15 degree jump on the field and on the retina. After completion of that saccade or sequence of saccades, suppose the target jumps horizontally to the opposite edge of the 30 degree field of view—the target will now be imaged on the retina 30 degrees away from the fovea, so 30 degrees is the radius of the region that can be mapped.

Accordingly, in exemplary embodiments, mapping may consist of placing a target at various places on the retina and observing the resulting eye movements. The eye movements may indicate whether or not the various positions on the retina are healthy. In exemplary embodiments, the resulting data may include retinal points that were not initially selected for mapping. Suppose, for example, that the image of the target jumps to a blind region of the retina. The patient may make an initial eye movement that is incorrect, followed by one or more movements until the target is correctly fixated. After the initial movement, the image of the target now falls on a different region of the retina (e.g., a region not necessarily among those that were intended to be tested). If the patient then makes a correct eye movement, that region of the eye can be scored as "healthy" or "seen", and if, instead, still another eye movement occurs, that region of the retina can be scored as "not healthy" or "not seen".

In exemplary embodiments, it may be desirable to add target positions into the sequence of targets that are not in the set originally intended to be tested. For example, the patient may be looking at a point 10 degrees to the right of the center of the display, and the next point to be tested may be more than 5 degrees to the right of the fovea. Because the field of view has a radius of only 15 degrees, the next target will not fit within the field of view of the display. Instead, a new target position, e.g., 10 degrees to the left of center, may be inserted into the sequence and the patient may look at that point and then the desired point can be reached.

In exemplary embodiments, the patient's eye movements may be saved to construct a visual field map. During the procedure, the processor may abruptly move the target every T seconds (e.g., 0.2, 0.3, 0.4, 0.5, 0.6, 0.7, 0.8, 0.9, 1, 1.25, 1.5, 1.75, 2, 3, 4, 5, 6, 7, 8, 9, or 10 seconds) in such a way that, by the end of the procedure, the target has jumped to the locations on the patient's retina that were desired to be tested.

As discussed above, in exemplary embodiments, the location of the target on the display may be selected to correspond to a desired location of the patient's retina. Accordingly, in exemplary embodiments, the processor may need to be aware of two different surfaces and their different coordinate systems. One surface is the surface of the display within the instrument; the other is the surface of the patient's retina. When the patient looks at the target, the patient's external eye muscles rotate their eyes until the retinal image of the spot falls on the fovea. In exemplary embodiments, the device may continuously track the patient's direction of gaze with respect to the display. That is, the locations of the fovea and of the other points on the retina are known with respect to the display and a mapping between the patient's retina and the display is established. Since the display maps to some area of the retina that will be smaller than the entire retina, if it is desired to test whether a particular point of the retina is sensitive to light, the system first computes whether or not the point to be tested is within the area mapped to the display. If it is not, then it cannot be tested yet (but may be later, as explained below). If the retinal point to be tested does correspond to a point on the display, then the target can be moved to that point on the display, thus jumping the retinal image of the target on to the point on the retina that is to be tested.

As discussed above, if the point on the retina is sensitive to light (and if the patient is following the appropriate instructions), the patient will make what is called a "saccadic" eye movement. Specifically, after a minor delay, the eyeball will abruptly begin to rotate in a single very fast movement and will abruptly stop rotating in a position such that the retinal image of the test spot will again fall on the fovea. This kind of movement is ballistic. During the approximately 200 milliseconds after the target moves to the new position but before the eye begins to move, the brain computes the extent to which it must change the tensions in each of the eye muscles. The results of those calculations are then abruptly sent to the muscles, which execute the commands in the next few milliseconds. As a consequence, once a saccadic eye movement has been initiated, it will run its predetermined course. For example, if the stimulus spot jumps from A to B and then, while the saccade to B is occurring, the target moves to C, the eye will pause at B, wait about 200 milliseconds, and then make a new saccadic movement to C.

In contrast, if the target jumps to a spot on the retina that is insensitive to light, the following events may occur. The target may disappear from the patient's vision, and as a consequence, after a 200 millisecond delay, the patient may actually make a saccadic eye movement, but its direction and amplitude may be independent of the actual location of the test spot. This saccadic movement will shift the retina under the image of the target and so, when the saccadic movement ends, the image of the target may fall on some new region of the retina, and that region may be light-sensitive. Therefore, after another 200 milliseconds, the patient may make a new saccadic eye movement in such a direction and amplitude that the image of the target falls on the fovea.

Therefore, if a target moves to a new location and the eye is being accurately tracked, the sensitivity of the retinal location to which the target moved may be revealed. That is, if a single saccadic movement brings the eye to correctly fixate on or close to the spot, the location on the retina was responding to the target. If such a single movement did not occur, the retinal location may have a sensitivity too low to detect the target.

In exemplary embodiments, the patient may experience a trial in which a target jumps every few seconds to a new, apparently randomly selected location, and every once in a while, the spot may appear to briefly turn off. If the direction of gaze of the eye is constantly and accurately tracked, then it may be possible to know the mapping between the spatial coordinates of the retina and those of the display screen. That is, one can decide to test the sensitivity of any point on the retina that is mapped to within the area of the display and present a test flash at a location on the display that will correctly deliver the image of the target to the retinal point to be tested.

As discussed above, the eye movement perimeter device may consist of three subassemblies, one that tracks the patient's eye, a second that displays targets on a display, and a third, that controls the actions of the other two and/or the user interface.

In exemplary embodiments, the process for measuring a patient's perimetry may begin with an operator entering the patient's data (e.g., ID number, name, and any other desired data). The operator may select the form of the test to be performed, such as a "quick glaucoma screener". The operator then asks the patient to rest against a head-positioning device, which may consist of a forehead rest, nose bridge rest, or a chin rest, and look into the instrument at a small flashing spot of light straight ahead. An image of the region including the front of the patient's eye may appear on the operator's screen, the operator may use a mouse to drag the image until the pupil is roughly centered in a window, and then initiate the test. In exemplary embodiments, the remaining portion of the test may proceed automatically (or in a semi-automated manner in which e.g., an operator may mark out regions of the retina to return to for further analysis, e.g., mapping in finer detail any blind spots), under the control of the internal processor. The device may examine the image of the eye and find markers for its direction of gaze. For example, in an implementation, the center of the pupil and the location of the image of a light source formed by reflection from the cornea may be computed and the relative positions of the two may define the direction of gaze. As would be readily understood by persons of skill in the art, there are several eye-tracking methods available and the particular one used may be immaterial so long as it provides a measure not merely of the location of the eye but rather of the angular position of the eye, that is, the direction of gaze.

The target then suddenly jumps to a new position on the display, one that corresponds to one of the locations on the retina that is to be tested. After a delay of duration to be determined but of approximately two seconds, the eye will have moved to a new direction of gaze that corresponds to the new display stimulus position, thus shifting the mapping between the display and the retina. The internal computer evaluates whether or not the first saccadic movement was essentially correct and records that data. The processor then identifies another of the retinal locations to be tested, one that maps to some location on the display, and jumps the stimulus to that new position. This general procedure continues until the retinal locations to be tested have been stimulated. The same process occurs for any additional saccades that occur before the new target is fixated.

Figure 2:
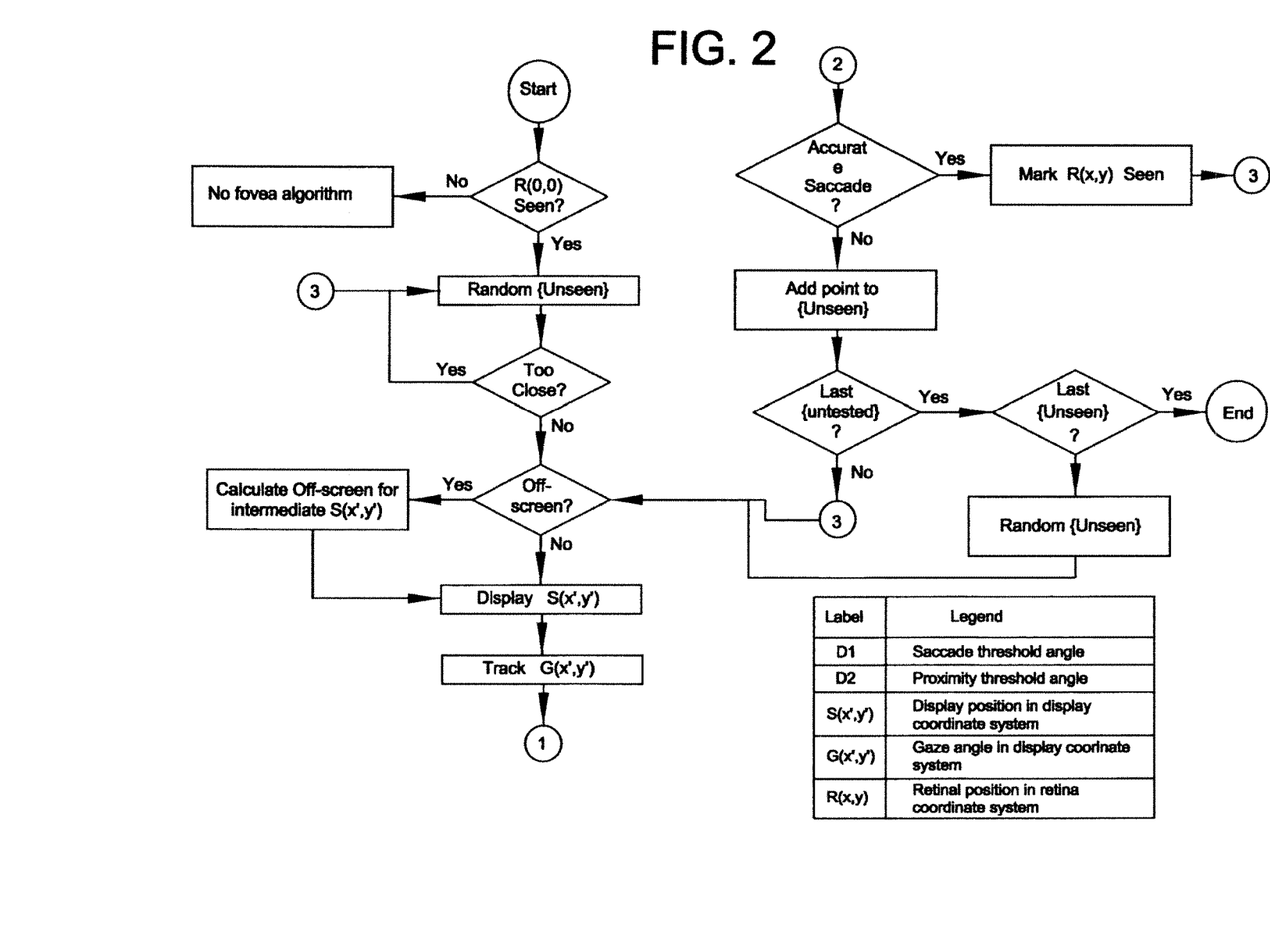
FIG. 2 is a flow chart describing an exemplary process for monitoring and/or measuring eye movement in response to stimuli provided on a display.

FIG. 2 is a flow chart describing an exemplary process for monitoring and/or measuring eye movement in response to stimuli provided on a display. In exemplary embodiments, the process for measuring eye movement may begin by creating a table (or list) of retinal positions to test. The table may comprise a column for "Tested", another for "Seen", another for "not seen once", another for "not seen twice." The table may be referred to as a "map table." A "saccade" may be defined as a single movement that begins and ends with movement smaller than M degrees during e.g., a 100 msec period and a correct saccade may be defined as a saccade with a gaze direction ending within a predefined number of degrees (D) of the target on the display.

With this initial set-up, the process exemplified in FIG. 2, begins by displaying the target in the middle of the display. The location on the display where the patient is looking is recorded. In the next step, a next retinal location from the map table is randomly selected from a group of positions in the set comprising the untested positions and the unseen positions. Based on the selected retinal location and the current gaze direction of the patient, the process continues by computing a corresponding location for the target on the display. If the target is too close to the previous target, the process will select a new target. If the target corresponds to a location that is off the display, the process continues by calculating an off screen position as described with respect to FIGS. 3A and 3B. If the target is not too close and on the display, the target is displayed and the movement of the patient's eyes are tracked. Next a determination is made as to whether the saccade was an accurate movement and if it was, the process records that the target was seen for the corresponding retinal position. If the saccade is not accurate, the position is marked as having been tested but not seen. In addition, in exemplary embodiments, it may be possible to obtain additional information from the incorrect saccade. For example, if there are more than two saccades (i.e., a initial movements to an incorrect location and last movement to the correct location), each of the retinal positions of the targets that produce the initial incorrect movements may be recorded as not seen retinal locations. In exemplary embodiments, it may be desirable to test unseen positions twice before concluding that the position is a blind spot. Accordingly, if the position is unseen for the first time, it may be added to the group of unseen positions so it can be tested again at a later, random time.

After all of the positions in the untested group and the unseen group have been tested, the test may conclude.

In exemplary embodiments, it may be desirable to perform threshold perimetry testing. In this case, the map table may be expanded such that, instead of just the points to be tested being listed in the table, the points are listed with a plurality (e.g., 2, 3, 4, 5, 6, 7, 8, 9, and/or 10) of corresponding brightnesses, sizes, shapes, colors, backgrounds, or other variations. In this manner, a single point may be expanded to a plurality of points having the same location but varying brightnesses, shapes, colors, backgrounds, or other variations.

In exemplary embodiments, it may be desirable to perform scotoma mapping. In this embodiment, a standard map table may be set up and perimetry performed as described above. However, if a "not seen" point is identified, a new set of points may be added to the table that lie in a circle D degrees (for example 1, 2, 3, 4, and/or 5 degrees) from the "not seen" point. If any of those points are "not seen", further points are added on an arc D degrees in radius and in a direction away from the previously unseen point.

Figure 3A:
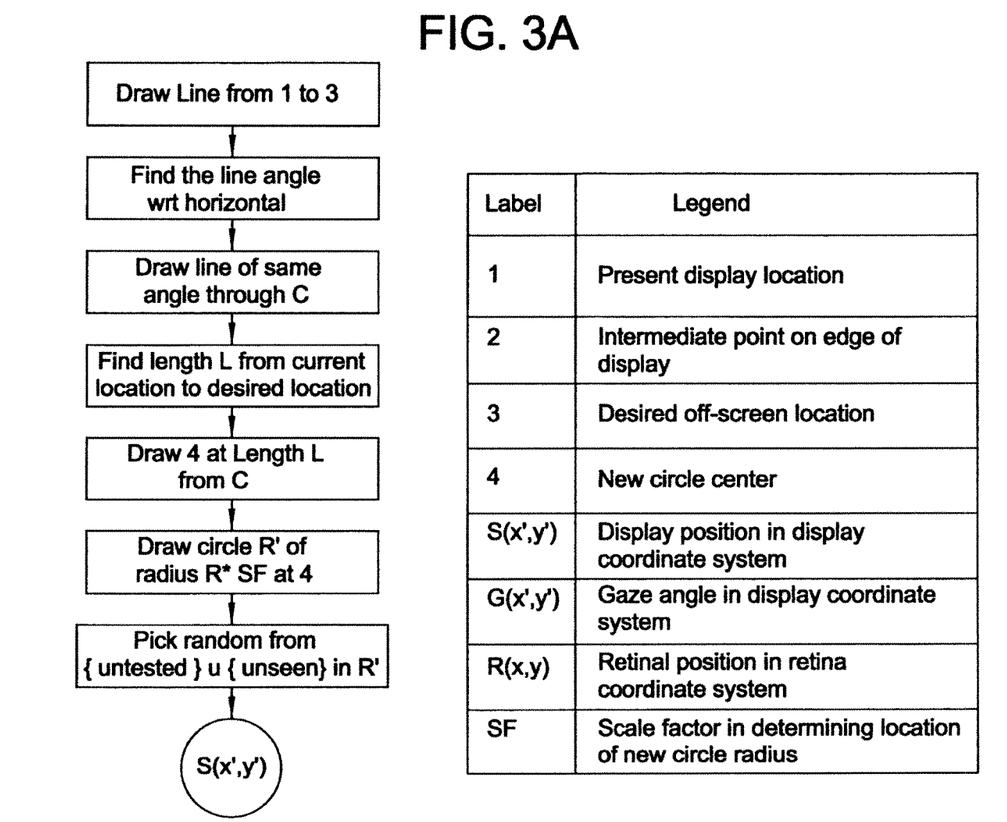
FIGS. 3A and 3B are diagrams describing an exemplary process for calculating off-screen positions of stimuli in accordance with the process described in FIG. 2.
Figure 3B:
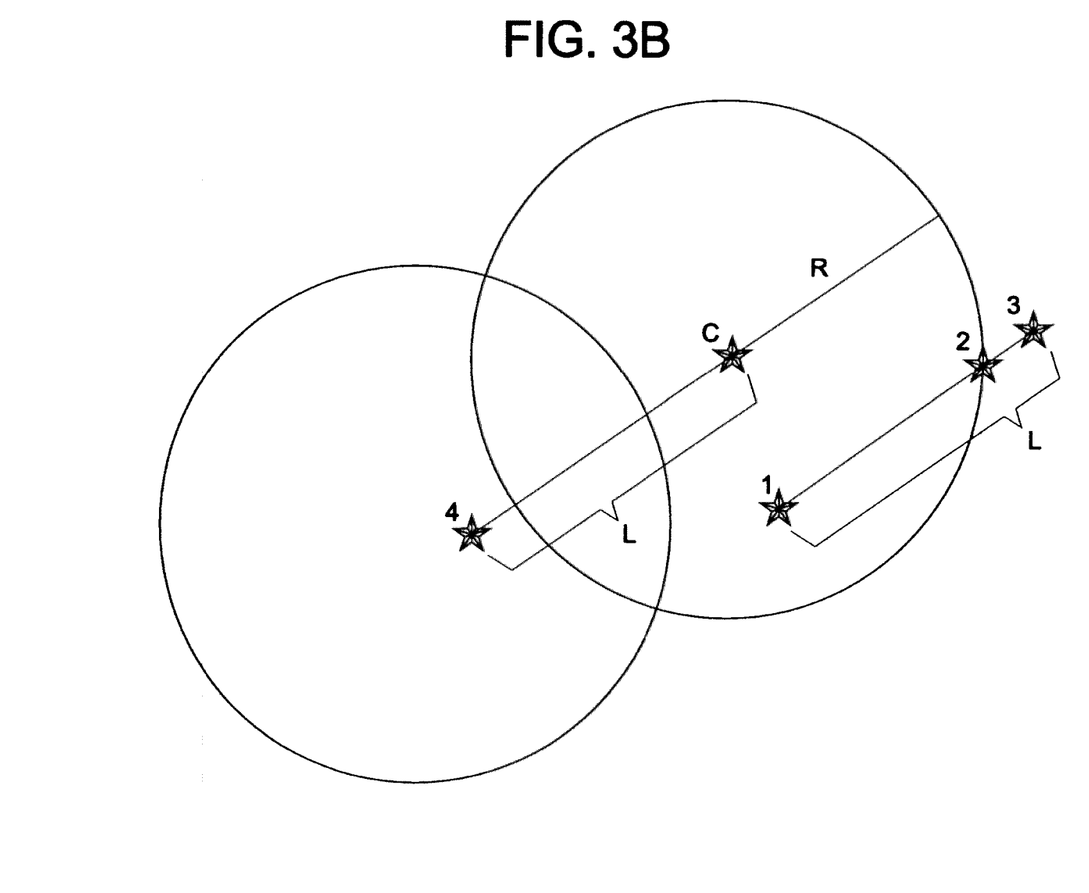

FIGS. 3A and 3B are diagrams describing an exemplary process for calculating off-screen positions of stimuli in accordance with the process described in FIG. 2. As discussed above, when a retinal position is selected, a corresponding position to display the target on the display is calculated to test that retinal position. In some instances, the calculated position may not lie on the display itself. Accordingly, it may be necessary to rely on an intermediate point. As illustrated in FIGS. 3A and 3B, a present display location (1), an intermediate point on the edge of the display (2) and a desired off screen point (3) are identified. Using this information, it may be possible compute the distance (L) from point (1) to point (3) and compute the angle (relative to a horizontal). Next, using this information, a new point (4) is identified. Point 4 is on a line at the same angle and at a distance from point (C—e.g., Center of the Display) that equals the distance from point 1 to point 3 and passes through point (C). Using this new position (4), the process can create a circular area centered around point (4) with a radius of R*SF (where R is the radius of the display and SF is a scale factor to ensure the point lies on the display). Then an intermediate point is randomly selected. If the intermediate point is contained within the intersection of the space within the display and the circular area defined around point (4), then it is used as the next target position. The patient moves their gaze to the intermediate position and then from that position, a new position on the display is calculated corresponding to the originally selected retinal position.

In exemplary embodiments, the process may comprise multiple tests that may have more or less points tested in a wider or narrower visual field angle, e.g., the Humphrey 30-2 visual field test tests 30 degrees around the fovea while the 10-2 visual field test tests 10 degrees around the fovea (a central vision test). In exemplary embodiments, it may be desirable to test a small number (e.g. 10 points per quadrant=40 points) or a much larger number (70-100+) of points. It may also be desirable to irregularly sample the grid (e.g., have a non-uniform sampling such that the test can more heavily sample regions of interest, e.g., blind spots).

In exemplary embodiments, when the target moves and the patient is correctly fixating it (within some predefined degree of accuracy), a tone may be sounded. Further, the first number of trials may be regarded as training trials to acquaint the patient with the task and to make sure the patient is able to perform it. For example, there may be occasional patients who, due to brain or muscle pathology, are unable to make accurate saccadic movements.

In exemplary embodiments, if the procedure reveals one or more retinal locations that did not trigger an accurate saccadic movement, those locations may be automatically retested during trials that are imbedded into the stimulus sequence.

In exemplary embodiments, when such a sequence is complete, the device may display and/or print a map showing the sensitivities of the various points on the retina that have been tested.

In exemplary embodiments, there may be one or more advantages to using this method over conventional perimetry methods. For example, the information about whether or not each point tested is seen may be determined more objectively. Accordingly, the patient doesn't need to make any judgments. In exemplary embodiments, the described procedure may be more natural to the patient because they do not have to decide whether or not a target was seen when it was not where he or she was looking. As a result, in exemplary embodiments, patient anxiety may be reduced and/or the results of the tests may be less variable. Using the standard procedure, the patient tries to look steadily at a stationary target straight ahead while looking for flashes off to the sides. Since the patient may not be looking at the stationary target when the test flash is delivered the flash may not be delivered to the place on the retina that was intended to be tested, and an erroneous datum may be be produced on the visual field map. However, as described in connection with the exemplary methods, when the direction of gaze is tracked and the target is positioned in accordance with that direction, then the point tested on the retina is known and is the one intended to be tested. Therefore, erroneous trials are eliminated (or at least significantly reduced) and the resulting visual field maps are more accurate.

Some perimeters that use the standard procedure include some form of eye tracking, such as a video camera that images the eye and displays an image which the operator can watch. If the operator notices that the eye appears not to be pointed correctly during a trial, the operator usually just uses the information to remind the patient to fixate on the target, and in some instruments he or she can signal the perimeter to ignore that trial. The procedure described herein does not require rejection of trials, and so may be more efficient and thus faster.

In exemplary embodiments, the device may be configured such that the position of the new stimulus on the retina is known. Specifically, the device may determine where the patient is actually looking, that is, where the retinal coordinates are with respect to the coordinates of the display, and then determine where on the display to place the next target so that it will actually fall on the retina in the location that is desired.

In exemplary embodiments, the position of the next target may be selected such that it appears random to the patient. In this manner, the patient is unable to predict where the next target will be. Additionally, in exemplary embodiments, the target may not jump back to the same place after the new position is tested—it just jumps to the new, unpredictable (to the patient) position. At least one previously described attempt to do perimetry by evaluating eye movements has the target jump back to the center after each new spot is tested. It has been realized that when the target jumps back to a center position after each new position is tested, patients may simply keep looking at the center and wait for the target to jump back there. The tendency to do that may be very hard to overcome even if the patient tries to resist it.

In exemplary embodiments, if the patient's eye movements indicate that he or she did not see the target when it jumped to a particular position, then a second test for that spot on the retina, may be automatically inserted into the testing sequence. In exemplary embodiments, the second test may be inserted in a manner that causes it to appear unpredictable/random to the patient.

In exemplary embodiments, the general procedure described herein may be performed with a variety of different types of targets and retinal locations. For example, the target spot can always have the same intensity or it may have varying intensities. In the case of a fixed intensity, the sensitivity map may, at the points tested, be binary, and if the brightness is set so that a patient with a healthy visual system will see all the points except those in the optic disk, the map will indicate blind spots, called scotomas. Alternatively, the targets can be delivered at a range of brightnesses, and the sensitivity map may become three-dimensional, for example, with height indicating the intensity necessary for the target to be seen.

In exemplary embodiments, the number and distribution of the tested points can also be varied. For example, just twenty points, in regions most likely to be affected by glaucoma, can be tested as a quick glaucoma screening.

In general, the target can be any color. For example, the target may be a small white spot on a dark display or, for specialized testing, the spot may be blue on a yellow background.

In exemplary embodiments, one eye may be tested at a time and both eyes may be tested in the same session.

In exemplary embodiments, the systems, devices, and methods described herein may be beneficial in diagnosing and/or monitoring progression of various diseases that affect the visual field. The eye is composed of three primary structures—the cornea, the lens, and the retina. Light travels through the cornea and lens to the retina to be sensed by the retina. Trauma or disease can obstruct the path of light through the eye. For example, corneal scarring (e.g., due to trachoma) or clouding of the lens (e.g., due to cataract) may obstruct the path of light to the retina. The retina is composed of a layer of photosensitive cells and signal transduction and processing layers. Light is transduced from photons into neural signals at the photosensitive layer (the photoreceptors). The signal from many photoreceptors is passed to fewer bipolar cells, which then pass to even fewer ganglion cells. This many-to-one relationship provides some of the early processing of visual information before light is conducted to the brain. Damage to any of these layers can create a portion of the eye that is not able to properly transduce light into neural signals.

In exemplary embodiments, the systems, devices, and methods described herein may be beneficial in diagnosing and/or monitoring progression of glaucoma. Glaucoma is a neuro-degenerative disease in which the ganglion cells die. This can cause regions of visual field loss, typically in the superior and inferior aspects of the eye. Glaucoma may be detectable with the described systems, devices, and methods.

In exemplary embodiments, the systems, devices, and methods described herein may be beneficial in diagnosing and/or monitoring progression of retinal artery or vein occlusion. Blood vessels in the eye can become partially or completely occluded by a thrombosis, leading to regions of the retina that are not perfused. Lack of perfusion (i.e., ischemia), which can lead to regions of tissue death and visual field loss. These issues may be detectable with the described systems, devices, and methods.

In exemplary embodiments, the systems, devices, and methods described herein may be beneficial in diagnosing and/or monitoring progression of retinitis pigmentosa. Retinitis pigmentosa is a disease affecting the photosensitive cells in the eye, the rods and cones. RP is typically characterized by peripheral vision loss leading to tunnel vision as the rod cells in the eye are lost. Some types of retinitis pigmentosa affect the cone cells as well and can lead to progressive, total visual field loss. These issues may be detectable with the described systems, devices, and methods.

In exemplary embodiments, the systems, devices, and methods described herein may be beneficial in diagnosing and/or monitoring progression of hemianopsia and optic tract glioma. Hemianopsia and optic tract glioma are conditions in which half or more of the visual field is lost due to trauma or disease (typically a lesion or tumor). In hemianopsia, half of the visual field will be lost in both eyes, e.g., the right half of the field in both eyes. Lesions in the brain can even lead to quadrantopsia, in which one quadrant of the visual field will be missing from both eyes. These issues may be detectable with the described systems, devices, and methods.

In exemplary embodiments, the systems, devices, and methods described herein may be beneficial in diagnosing and/or monitoring progression of retinal detachment. Disease or trauma can lead to a retinal detachment, a condition in which some or all of the layers of the retina pull away from other tissues of the eye. Vision loss occurs at the site of the detachment. This issue may be detectable with the described systems, devices, and methods.

In exemplary embodiments, the systems, devices, and methods described herein may be beneficial in diagnosing and/or monitoring progression of multiple sclerosis. Optic neuritis associated with multiple sclerosis may lead to partial or full blindness in one or both eyes. These issues may be detectable with the described systems, devices, and methods.

While exemplary embodiments have been shown and described herein, it will be obvious to those skilled in the art that such embodiments are provided by way of example only. It is intended that the following claims define the scope of the invention and that methods and structures within the scope of these claims and their equivalents be covered thereby.

What is claimed is:

1. A method for evaluating retinal function and testing the visual field of a patient by monitoring how the patient tracks a target image on a display, the method comprising:
    displaying the target image on the display, the target image being located at a first position on the display such that it is visible to the patient;
    identifying what portion of the display the patient is looking at;
    selecting a location of the patient's retina to test;
    calculating, based at least in part on what portion of the display the patient is looking at, a second position on the display corresponding to the selected location of the patient's retina;
    displaying the target image at the second position on the display;
    identifying how many eye movements the patient made to look at the target at the second position; and determining, based at least in part on the number of eye movements, whether the patient was able to see the target at the second position;

wherein if the patient makes more than one eye movement (e.g., more than one eye movement of M degrees) to look at the target at the second position from the first position, the process identifies the intermediary positions where the patient was looking and determines, based at least in part on the next eye movement, whether the patient was able to see the target when the eye was at the intermediary positions.

2. The method of claim 1, wherein the selection of the location on the patient's retina is perceived as being random by the patient.

3. The method of claim 1, wherein the process continues by displaying the target image at a predetermined plurality of positions on the display corresponding to predetermined positions of the patients retina until a map of the patient's retina is achieved.

4. The method of claim 1, wherein, if the patient makes a single eye movement to look at the target at the second position from the first position, the determination is made that the patient was able to see the target at the second position.

5. The method of claim 1, wherein, if the patient makes more than one eye movement to look at the target at the second position from the first position, the determination is made that the patient was not able to see the target at the second position.

6. The method of claim 1, wherein if the patient make more than one eye movement to look at the target at the second position from the first position, the process re-tests the second position on the retina of the patient.

7. The method of claim 1, further comprising adjusting the distance of the display relative to the patient to focus the target.

8. The method of claim 1, wherein the target jumps from the first position on the display to the second position on the display.

9. The method of claim 1, wherein the target jumps from the first position on the display to the second position on the display after about 0.2, 0.3, 0.4, 0.5, 0.6, 0.7, 0.8, 0.9, 1, 1.25, 1.5, 1.75, 2, 3, 4, 5, 6, 7, 8, 9, or 10 seconds.

10. The method of claim 1, wherein the area of the patient's retina that is measurable is approximately twice the diameter of the patient's field of view on the display.

11. The method of claim 1, wherein there is only one target on the display at a time.

12. The method of claim 1, wherein any combination of the brightness, size, shape, color, or background of the target is variable.

13. The method of claim 1, wherein the process is used, at least in part, to aid with diagnosing and/or monitoring progression of glaucoma.

14. The method of claim 1, wherein the process is used, at least in part, to aid with diagnosing and/or monitoring progression of diabetic retinopathy.

15. The method of claim 1, wherein the process is used, at least in part, to aid with diagnosing and/or monitoring progression of retinal artery or vein occlusion.

16. The method of claim 1, wherein the process is used, at least in part, to aid with diagnosing and/or monitoring progression of retinitis pigmentosa.

17. The method of claim 1, wherein the process is used, at least in part, to aid with diagnosing and/or monitoring progression of hemianopsia and optic tract glioma.

18. The method of claim 1, wherein the process is used, at least in part, to aid with diagnosing and/or monitoring progression of retinal detachment.

19. A method for evaluating retinal function and testing the visual field of a patient by monitoring how the patient tracks a target image on a display, the method comprising:

displaying the target image on the display, the target image being located at a first position on the display such that it is visible to the patient;

identifying what portion of the display the patient is looking at;

selecting a location of the patient's retina to test;

calculating, based at least in part on what portion of the display the patient is looking at, a second position on the display corresponding to the selected location of the patient's retina;

displaying the target image at the second position on the display;

identifying how many eye movements the patient made to look at the target at the second position; and determining, based at least in part on the number of eye movements, whether the patient was able to see the target at the second position;

wherein the target jumps from the first position on the display to the second position on the display after about 0.2, 0.3, 0.4, 0.5, 0.6, 0.7, 0.8, 0.9, 1, 1.25, 1.5, 1.75, 2, 3, 4, 5, 6, 7, 8, 9, or 10 seconds.

20. The method of claim 19, wherein the process continues by displaying the target image at a predetermined plurality of positions on the display corresponding to predetermined positions of the patients retina until a map of the patient's retina is achieved.

* * * * *